United States Patent [19]

Buell

[11] 4,147,580
[45] Apr. 3, 1979

[54] METHOD OF BONDING A POROUS FIBROUS WEB TO A SUBSTRATE

[75] Inventor: Kenneth B. Buell, Cincinnati, Ohio

[73] Assignee: The Procter & Gamble Company, Cincinnati, Ohio

[21] Appl. No.: 792,523

[22] Filed: May 2, 1977

Related U.S. Application Data

[62] Division of Ser. No. 627,406, Oct. 30, 1975, Pat. No. 4,069,822.

[51] Int. Cl.² .................. B32B 7/14; B32B 31/10
[52] U.S. Cl. .................... 156/291; 128/287; 156/295; 156/301; 156/548; 156/549; 156/578; 428/198
[58] Field of Search ............... 156/291, 309, 269, 295, 156/301, 549, 548, 555, 578, 582; 428/198, 246, 245; 128/287, 290 P, 284

[56] References Cited

U.S. PATENT DOCUMENTS

| | | | |
|---|---|---|---|
| 1,831,403 | 11/1931 | Woodward | 156/548 |
| 3,505,083 | 4/1970 | Schelhorn | 128/287 |
| 3,636,952 | 1/1972 | George | 128/287 |
| 3,695,985 | 10/1972 | Brock et al. | 156/291 X |
| 3,716,434 | 2/1973 | Cook et al. | 156/291 |
| 3,860,003 | 1/1975 | Buell | 128/287 |
| 3,860,004 | 1/1975 | Nystrand | 128/287 |
| 3,924,626 | 12/1975 | Lee et al. | 128/287 |
| 3,984,272 | 10/1976 | Teed | 156/291 |

*Primary Examiner*—Michael G. Wityshyn
*Attorney, Agent, or Firm*—Melville, Strasser, Foster & Hoffman

[57] ABSTRACT

A method of bonding a fluid-porous, fibrous, woven or non-woven web to a substrate and products made thereby. The porous web is overall or pattern coated with an extremely low level of hot-melt adhesive by causing the hot-melt adhesive to be wiped from a controlled thickness hot-melt adhesive source by the individual projecting surface fibers and fiber junctions of the porous web. Hot-melt adhesive globules are formed on the individual projecting surface fibers and fiber junctions which, when the porous web and substrate are passed through a preset clearance nip roll assembly, provide a product wherein the porous web is bonded to the substrate with excellent bond strength, the porous web remaining flexible and completely transparent to fluid transmission.

14 Claims, 8 Drawing Figures

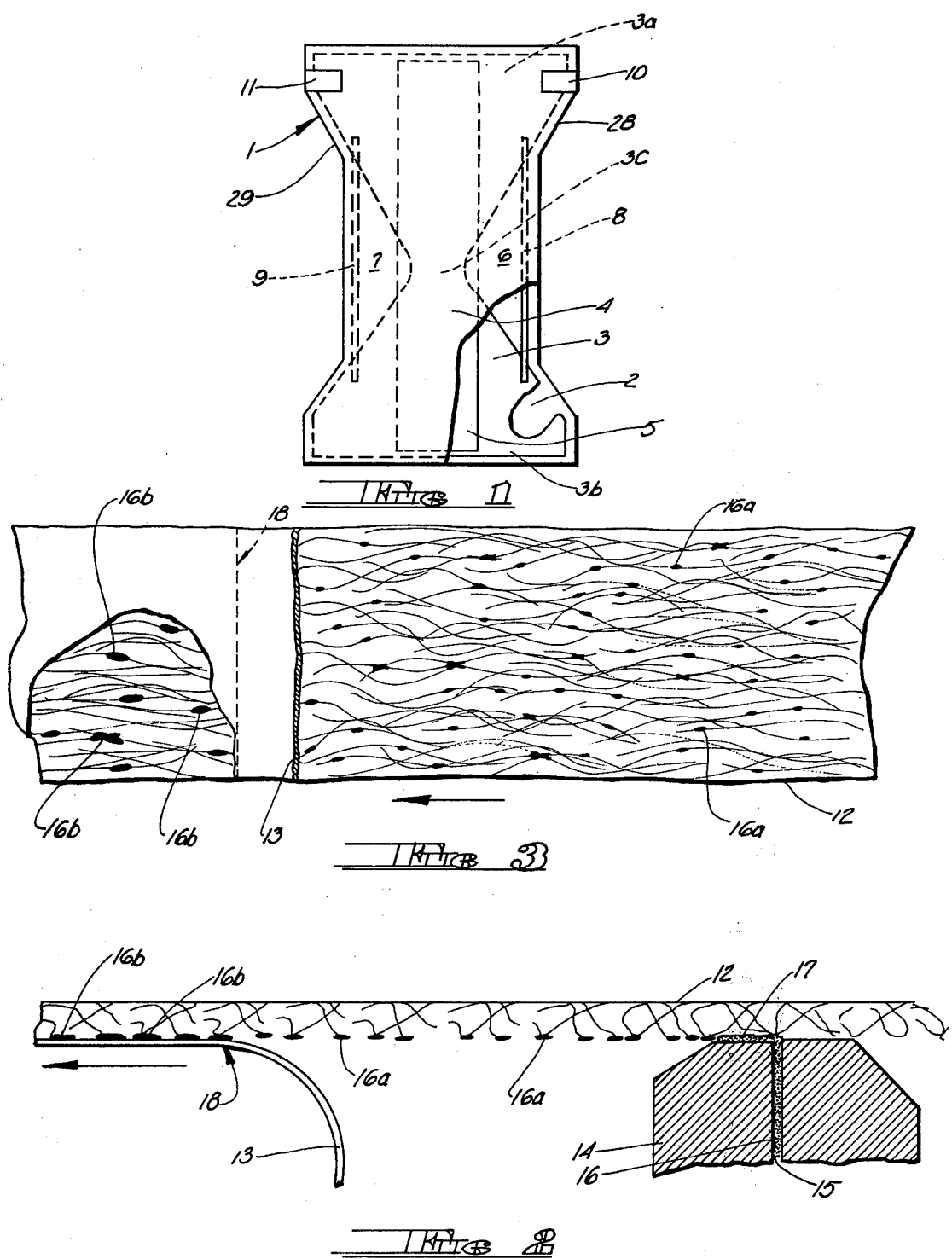

METHOD OF BONDING A POROUS FIBROUS WEB TO A SUBSTRATE

CROSS REFERENCE TO RELATED APPLICATION

This is a division of application Ser. No. 627,406, filed Oct. 30, 1975, now U.S. Pat. No. 4,069,822, issed Jan. 24, 1978, in the name of the same inventor and entitled A METHOD OF BONDING A POROUS FIBROUS WEB TO A SUBSTRATE AND ARTICLES MADE THEREBY.

BACKGROUND OF THE INVENTION

1. Field of the Invention

The invention relates to a method of bonding a porous fibrous web to a substrate and articles made thereby, and more particularly to a process whereby and products wherein a porous web is affixed to a substrate with excellent bond strength utilizing a very low level of hot-melt adhesive, the bond being essentially invisible and the porous web maintaining its flexibility and fluid transparency.

2. Description of the Prior Art

The process of the present invention may be applied in any instance where it is desired to provide a laminated product, at least one lamination of which comprises a fluid-porous, fibrous sheet. An excellent example of such a product is an integral disposable diaper. While not intended to be so limited, for purposes of exemplary showing the present invention will be described in its application to the manufacture of integral disposable diapers.

Prior art workers have devised a number of different types of integral disposable diapers. Generally, however, such diapers comprise three basic parts: a moisture pervious topsheet intended to lie adjacent the body of the wearer, a moisture proof backsheet and an absorbent core therebetween. Examples of such disposable diapers are taught in U.S. Pat. Nos. Re. 26,151 and 3,860,003. The absorbent core may or may not be provided with a layer of high wet strength tissue on one or both of its faces.

In a typical practice, a topsheet may be provide with an extruded bead or stripe of hot-melt adhesive along each of its edges. These edges are folded about the edges of the absorbent core and are adhered to the underside of the absorbent core. In somewhat similar fashion, extruded hot-melt adhesive stripes or beads are located on the backsheet inset from and parallel to its longitudinal edges. The folded edges of the topsheet are adhered to the backsheet by means of these last mentioned adhesive stripes. Additional adhesive stripes or beads may be provided on the topsheet to join it to the backsheet at the waste band areas of the diaper.

In another approach, the backsheet is provided with a plurality of longitudinally extending hot-melt adhesive stripes or beads in parallel spaced relationship. The absorbent core is applied to the backsheet and adhered thereto by the adhesive stripes. The topsheet is next applied, being adhered to those edge portions of the backsheet which extend beyond the core.

The above approaches utilizing hot-melt adhesive stripes or beads result in certain deficiencies. First of all, the adhesive usage is relatively high with respect to the area actually bonded and the adhesive stripes or beads are apparent and unsightly. At the positions of the adhesive stripes or beads, the softness of the product is reduced. As a result, much work has been directed to making the stripes or beads of hot-melt adhesive as thin as possible so as to be as flexible as possible. Wherever the adhesive stripes or beads are applied to, or are in contact with, the porous, fibrous topsheet, the porosity of the topsheet is lost or seriously effected. Furthermore, in products requiring large areas of bonding a multiplicity of adhesive stripes are required in close proximity thereby greatly exaggerating the above enumerated deficiencies. Finally, in those prior art approaches wherein only peripheral gluing of the diaper components is practiced, the absorbent core may shift or bunch due to movement of the wearer.

The present invention provides a process whereby and a product wherein a hot-melt adhesive may be applied to even large areas of the porous, fibrous topsheet and the topsheet adhered to the substrate (the backsheet and/or the absorbent core). Hot-melt adhesive applied to the porous, fibrous topsheet in the manner taught herein provides an excellent fiber-to-adhesive bond with very good peel and creep bond characteristics to substrates. Nevertheless, the adhesive is substantially invisible; the softness of the product is retained and the moisture transparency-permeability of the topsheet is reduced only by 5% or less. Where the disposable diaper has cut longitudinal edges (as in diapers of the type taught in the above mentioned U.S. Pat. No. 3,860,003) the entire edge portions of the diaper can be laminated producing neater and more easily cut edges.

SUMMARY OF THE INVENTION

A product is made by laminating a fluid-porous, fibrous, woven or non-woven web to a substrate web. To this end, the porous web is pattern coated or coated overall with an extremely low level of hot-melt adhesive by causing the hot-melt adhesive to be wiped from the slot extrusion orifice of a glue nozzle (or other controllable-trickness adhesive source) by the individual projecting surface fibers and fiber junctions (i.e., junctions formed by overlapping or intersecting surface fibers) of the porous web.

The liquid, hot-melt adhesive tends to form globules on the projecting surface fibers and fiber junctions, which globules are characterized by excellent adhesive-to-fiber attachment. It will be understood that the globules need not necessarily be spherical and most frequently are elongated in the direction of the fibers to which they adhere and often in the direction of travel of the web. It has further been noted that at sites of surface fiber junctions the globules will be enlarged at the points of junction or cross-over of the surface fibers by virtue of surface tension or capillary effects. The porous, fibrous web is thereafter passed, together with the substrate web, through a preset clearance nip roll assembly whereupon the fibrous porous web becomes firmly bonded to the substrate web. In this way, a highly porous, fibrous web can be continuously adhesively coated and laminated to the substrate web. Very good bond strength is achieved and at the same time the moisture transparency/permeability of the porous, fibrous sheet is very little affected. The adhesive is essentially invisible and the flexibility and compliance of the final product is essentially unaffected.

To prevent the laminating hot-melt adhesive from pressing through the highly porous, fibrous web when being laminated to a substrate web, the laminating nip roll contacting the porous web may be double-wrapped by the porous web. This entails passing the porous web uncoated through the nip and then looping it back around and through the nip again, having been adhesive coated in the mean time. Any adhesive "press-through" occuring during the lamination operation will be transferred onto that portion of the uncoated fibrous web passing through the nip.

BRIEF DESCRIPTION OF THE DRAWINGS

FIG. 1 is a plan view of an exemplary disposable diaper in an unfolded configuration and partially fragmented.

FIG. 2 is a fragmentary, diagramatic view, partially in cross section, and illustrating the application of a hot-melt adhesive to a porous, fibrous web and the laminating of that web to a substrate.

FIG. 3 is a fragmentary, semi-diagramatic, magnified bottom view (partly in cross section) of a narrow portion of the porous, fibrous web and substrate of FIG. 2.

DESCRIPTION OF THE PREFERRED EMBODIMENTS

Figures 4, 5:
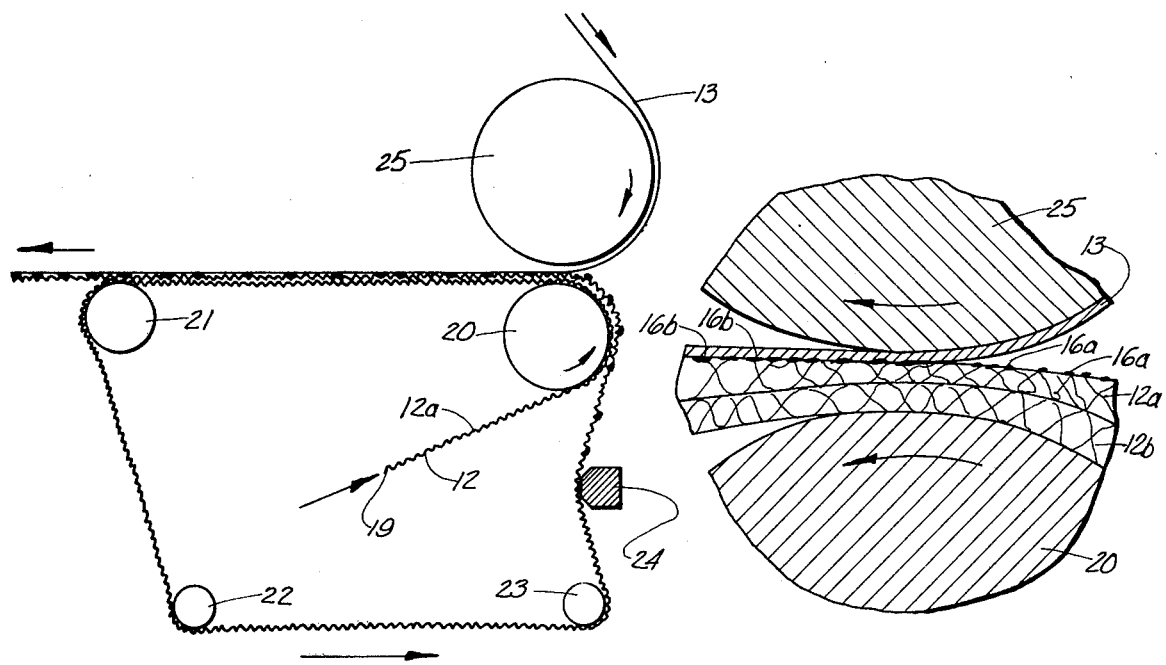
FIG. 4 is a semi-diagramatic side elevational view of a system for applying hot-melt adhesive to a porous, fibrous web and laminating the web to a substrate.
FIG. 5 is an enlarged, fragmentary, cross sectional view of the preset nip of FIG. 4.

As indicated above, the manufacture of disposable diapers constitutes an excellent application of the present invention, and, while not intended to be so limited, the invention will be described in terms thereof. To this end, an exemplary diaper of the type taught in the above mentioned U.S. Pat. No. 3,860,003 is shown in FIG. 1. The diaper, generally indicated at 1, is made up of three basic parts: a flexible, moisture impermeable backsheet 2, an absorbent core 3 and a porous, fibrous topsheet 4.

The moisture impermeable backsheet 2 may be made of any suitable material such as a low density, opaque polyethylene web having a thickness of about 0.0015 inch. The absorbent core 3 may be any of the absorbent materials known to those skilled in the art as for example a multiplicity of plies of crepe cellulose wadding, fluffed cellulose fibers, textile fibers, fluffed wood pulp (generally known as airfelt) or other absorbent materials. As a part of the core, a wet strength tissue layer may be applied to that face of the core adjacent backsheet 2, to that face of core 3 adjacent topsheet 4 or both. One such tissue layer is shown at 5.

Topsheet 4 may again be made of any suitable compliant, soft feeling, porous material. In general, a topsheet for a disposable diaper is made up of woven or non-woven fibers such as, for example, mixtures of polyester and rayon fibers.

In the embodiment illustrated, the absorbent core 3 is of an hour glass shape forming a back portion 3a, a front portion 3b and a crotch portion 3c. Between the back and front portions of absorbent core 3 and adjacent the crotch portion 3c the bottomsheet 2 and topsheet 4 are joined together to form side flaps 6 and 7. Elastic members 8 and 9 are operatively associated with side flaps 6 and 7, respectively, causing side flaps 6 and 7 to be gathered and to form a moisture proof seal with the wearers legs during use. The diaper of FIG. 1 may also be provided with attachment tapes 10 and 11, as is well known in the art.

In the assembly of such a diaper structure, it is common to present the backsheet 2 and topsheet 4 as continuous webs. Core elements 3 and elastic members 8 and 9 are appropriately located between the topsheet and backsheet webs and the webs are caused to be joined together. Heretofore, the joiner of these elements was accomplished by double coated pressure sensitive tape, beads or strips of hot-melt adhesive appropriately located on the topsheet web or the backsheet web or both, or by other attachment means or combinations of attachment means. These various attachment methods resulted in numerous deficiencies, as enumerated above.

In accordance with the present invention, attachment of the diaper parts is accomplished by applying hot-melt adhesive to the topsheet web and causing the topsheet web to become laminated to the absorbent core and those exposed portions of the backsheet web. The absorbent core may be additionally attached to the backsheet web by any appropriate means, if desired.

FIGS. 2 and 3 diagramatically represent the gluing and laminating of a porous, fibrous web to a substrate web. For purposes of an exemplary showing, a porous, fibrous non-woven web 12 is shown which may be equivalent to topsheet 4 of FIG. 1. Similarly, non-porous substrate web 13 is illustrated which again may be equivalent to backsheet 2 of FIG. 1. For purposes of clarity, core elements such as core element 3 of FIG. 1 and elastic elements such as elastic elements 8 and 9 of FIG. 1 are not shown in FIGS. 2 and 3.

A hot-melt adhesive is applied to the porous, fibrous web 12 by direct contact extrusion. To this end, a glue nozzle 14 is provided having a slot extrusion orifice 15. Hot-melt adhesive 16 is pumped through orifice 15 forming a small pool of adhesive 17. As the porous, fibrous web 12 is drawn over nozzle 14 and the adhesive pool 17, surface fibers and fiber junctions will "pick-off" adhesive from pool 17. In this way, adhesive globules 16a are formed on the surface fibers and fiber junctions having exellent adhesive-to-fiber attachment points. As shown in FIGS. 2 and 3, adhesive globules 16a are randomly located at the position of the fibers and fiber junctions at the surface of porous web 12. The porous, fibrous web 12 is thereafter immediately combined with the substrate web 13 and webs 12 and 13 are subjected to moderate compression forces at the point of combination, generally indicated at 18. This is accomplished by a preset clearance nip roll assembly, as will be described hereinafter. The hot-melt adhesive globules are deformed (i.e., slightly flattened and widened under compression as at 16b in FIGS. 2 and 3) to increase the total adhesive contact area to the substrate surface. This assures good adhesion to the substrate web 13. In instances where a cooled "skin" forms on the adhesive globules the term "deformed" is intended to include the rupturing of the globule "skin" under compression to expose the heated interior to the substrate.

The glue nozzle 14 is a conventional slot extrusion orifice nozzle well known in the art. Excellent results have been achieved, for example, through the use of such nozzles manufactured by Acumelt Labratories, Inc. of Newton Lower Falls, Mass.

Hot-melt adhesives having a wide variety of temperature characteristics and adhesive properties are readily available. It is well within the skill of the ordinary worker in the art to select a hot-melt adhesive having appropriate temperature, flow and adhesive characteristics for coating on the porous, fibrous web 12 and an application temperature to enable the adhesive globules to possess sufficient "open-time" (i.e., time to solidification) between the application of the adhesive to the porous, fibrous web 12 and the combining of web 12 with substrate web 13. For example, in applying a porous, carded non-woven fibrous topsheet web (of 70% to 100% polyester fibers of 1½ to 3 denier, 0% to 30% rayon fibers of 3 denier, and bonded together with 20% to 25% cross-linking vinyl acrylic latex, to achieve a total web basis weight of from 20 to 30 gm/yd$^2$ and having a thickness of from 0.008 to 0.020 inch) to a polyethylene backsheet web, excellent results have been achieved using a hot-melt adhesive manufactured by Findley Adhesives of Milwaukee, Wis., under the formulation number 690-334 at an application temperature of from about 280° F. to about 320° F. (with an open time of up to about 1 second).

It has been determined that for best results and for any desired web speed the hot-melt adhesive 16 should be pumped through the slot extrusion orifice 15 of nozzle 14 at a rate such that, if it were being applied to a smooth, non-fibrous web, a continuous, uniform adhesive layer of from about 0.0002 inch to about 0.0010 inch in thickness would be produced. This will result in globules on the surface fibers and fiber junctions of the porous, fibrous web of from about 0.001 inch to about 0.008 inch in thickness.

A system for adhesive coating the porous, fibrous web 12 and laminating it to the substrate web 13 is diagrammatically illustrated in FIG. 4. The web 12, from a source thereof generally indicated at 19 is caused to pass over a nip roll 20. The web 12 thereafter passes over additional idler rolls 21, 22 and 23. After its passage about roll 23 the web 12 is coated with hot-melt adhesive by causing it to pass over glue nozzle 24 equivalent to glue nozzle 14 of FIG. 2. The coated web 12 again passes about nip roll 20 at which time it is combined with substrate web 13 passing about nip roll 25 to produce the desired laminated web assembly. FIG. 5 is an enlarged view of the nip between rolls 20 and 25 it will be evident from this figure that that portion of web 12 provided with adhesive globules 16a (and indicated at 12a) passes through the nip between the substrate web 13 and the initial, unglued portion of web 12, indicated at 12b. This "double-wrapping" of web 12 about nip roll 20 will assure that during lamination any hot-melt adhesive pressed through the highly porous web portion 12a will be transferred onto the backup web portion 12b and will not accumulate on the laminating nip roll 20.

In the preferred practice of the system of FIGS. 4 and 5, idler roll 21 is so positioned that the unglued portion of web 12 will remain in contact with the glued portion of web 12 until the unglued web portion reaches idler roll 21. This will give any adhesive pressed through web portion 12a during its passage through the nip and contacting web portion 12b (see FIG. 5) an opportunity to solidify. While the amount of adhesive "press through" or "strike-through" will be very little, any points of joiner between the glued and unglued porous web portions will be cleanly broken at idler roll 21 without glue stringing or the like.

Combiner rolls 20 and 25 are set at a fixed, predetermined nip clearance. The preset nip gap should be such as to produce a soft compression force between the hot-melt adhesive treated porous, web 12 and the substrate web 13. As used herein, the phrase "a soft compression force" is intended to mean a force sufficient to deform the globules into intimate contact with the substrate web and rupture the surface film of the hot-melt adhesive globules 16a (if required) while minimizing "strike-through" or "press-through" of the adhesive. As an example, excellent results were achieved with a preset nip gap of 0.012 inch during the lamination of a porous, fibrous, carded non-woven web of the type described above and having a thickness of 0.016 inch (double wrapped about nip roll 20 for an effective uncompressed thickness of 0.032 inch) and a polyethylene substrate web of 0.0015 inch thickness, utilizing the adhesive formulation set forth above.

Figure 6:
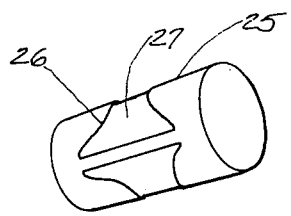
FIG. 6 is a perspective view of a modified form of that nip roll of FIG. 4 contacting the substrate.

When the system of FIGS. 4 and 5 is used in the manufacture of diapers of the type, for example, illustrated in FIG. 1, core elements 3 and elastic elements 8 and 9 will be introduced between the porous topsheet web 12 and the moisture proof backsheet web 13 prior to the passage of these webs through the nip of rolls 20 and 25. In such an instance, the roll 25 will, as shown in FIG. 6, have a peripheral cavity 26 configured to accept an absorbent core 3 as it passes between rolls 20 and 25. The cavity 26 may be filled with a resilient material 27 such as foam open pore urethane elastomer or the like. The cavity 26 is so sized and the resilient material 27 is so chosen that that portion of the web assembly containing an absorbent core is subjected to no greater compression force than that portion of the web assembly which does not have an absorbent core therebetween.

Once the core-containing web assembly has passed between the preset nip rolls 20 and 25 and beyond idler roll 21, the assembly may be cut into individual integral disposable diapers of the type shown in FIG. 1. The disposable diaper products, made in accordance with the above described process, are characterized by the fact that the topsheet 4 has been firmly bonded to the wet strength tissue element 5, those portions of the absorbent core 3 which extend beyond tissue 5 and those portions of backsheet 2 which extend beyond the core 3. The bonding of the topsheet 4 to the core 3 and its wet strength tissue element 5 markedly improves the tearing and balling strength of the core and tends to retain the core in its proper position during movement of the wearer. The topsheet 4 having been coated with a hot-melt adhesive, nevertheless remains completely transparent to moisture transmission. The disposable diaper structure is highly flexible, shows little evidence of any adhesive attachment means and has excellent bond strengths (both peel and creep). The fact that topsheet 4 is firmly bonded to backsheet 2 particularly in the areas of side flaps 6 and 7 makes the cutting of lateral notches 28 and 29 therein both neater and easier. Despite their lamination, however, the side flaps 6 and 7 remain highly flexible and compliant.

In the manufacture of integral disposable diapers of the type shown in FIG. 1, it has been found to be unnecessary to coat the topsheet 4 overall. The process described with respect to FIGS. 2 through 5 lends itself well to the use of direct web contacting, multi-slotted, hot-melt glue applicator nozzles (well known in the art) capable of applying the hot-melt adhesive in a pattern. A porous, fibrous topsheet web fragment having a pattern coating of hot-melt adhesive is illustrated at 30 in FIG. 7. The adhesive pick-up by the surface fibers and fiber junctions of web 30 is the same as described with respect to FIGS. 2 and 3. The web 30 is provided with relatively wide glue areas 31 and 32 along its longitudinal edges. The wide glue areas 31 and 32 are so sized as to incorporate a portion at least of the side flaps 6 and 7 (see FIG. 1). Between the wide glue areas 31 and 32 there are a plurality of narrow glue areas 33 extending longitudinally of web 30 and in parallel spaced relationship. The width of glue areas 33 and the spaces therebetween have been exaggerated in FIG. 7 for purposes of clarity. Excellent results have been achieved, for example, with glue areas 33 having a width of about $\frac{1}{8}$ inch separated by non-glue areas having a width of about $\frac{1}{4}$ inch.

Figures 7, 8:
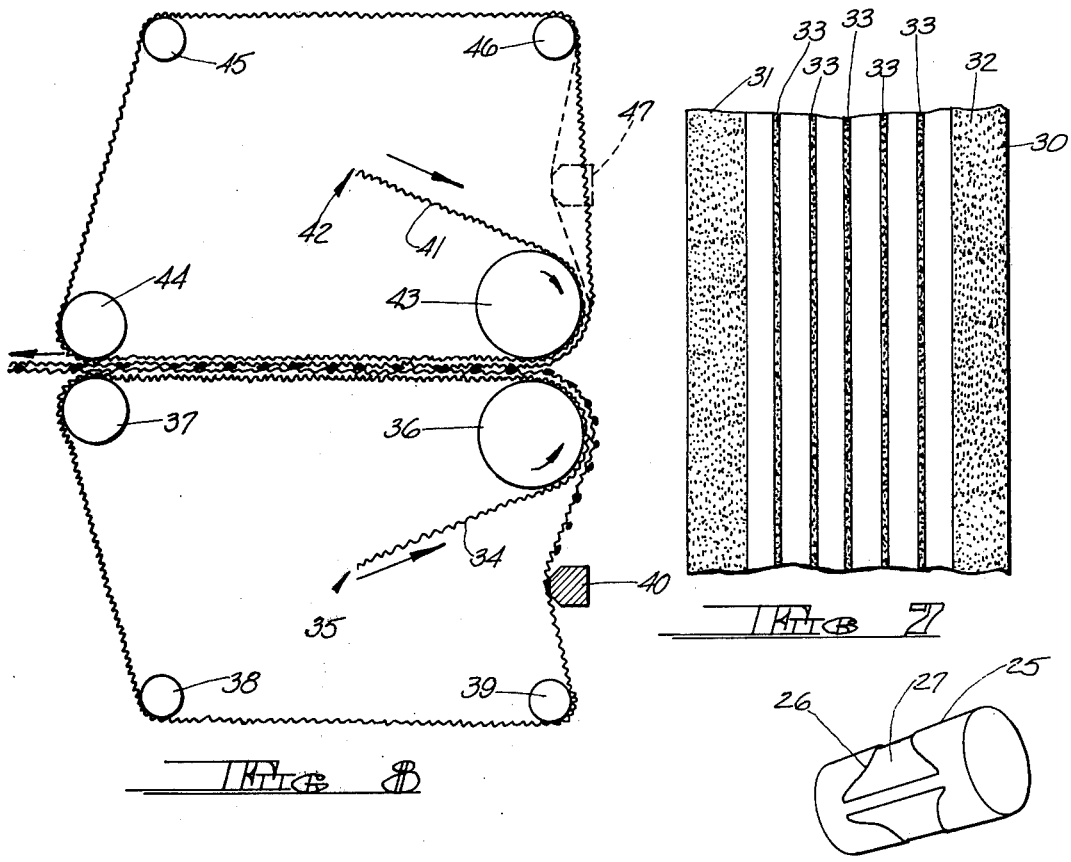
FIG. 7 is a fragmentary plan view of a porous fibrous web for use as a topsheet in the diaper of FIG. 1 and pattern coated with a hot-melt adhesive.
FIG. 8 is a semi-diagramatic elevational view of a system for applying hot-melt adhesive to a porous, fibrous web and laminating that web to a substrate in the form of a second porous, fibrous web.

A topsheet web of the type shown at 30 in FIG. 7 may be laminated to a backsheet web in the same manner described with respect to FIGS. 4 and 5. An excellent bond with all of the advantages described above is achieved with an even greater savings in the amount of hot-melt adhesive used.

The process illustrated in FIGS. 4 and 5 is applicable to the adhering of a porous, fibrous web to any suitable substrate web. FIG. 8 illustrates a system, similar to FIG. 4, wherein a porous, fibrous web is adhered to a substrate in the form of another porous, fibrous web. To this end, a first porous, fibrous web 34 from a source generally indicated at 35 is caused in unglued condition to pass about a nip roll 36 and a series of idler rolls 37 through 39. The rolls 36 through 39 are equivalent to rolls 20 through 23 of FIG. 4. After its passage about idler roll 39, the web 34 has a hot-melt adhesive applied thereto by a glue nozzle 40 equivalent to glue nozzle 24 of FIG. 4. Thereafter, the web again passes about nip roll 36.

A porous substrate web 41 from a source generally indicated at 42 is caused to pass about a second nip roll 43. Thereafter, web 41 passes over idler rolls 44 through 46 and again about nip roll 43 whereupon it is laminated with adhesive-coated web 34. The double wrapping of nip rolls 36 and 43 will prevent accumulation of hot-melt adhesive thereon in the same manner described with respect to FIG. 4. Again, it is preferred that idler rolls 37 and 44 be so located that the initial flights of webs 34 and 41 are stripped from the bonded web assembly 34-41 by these idler rolls, should any hot-melt adhesive strike through to the initial web flights. While for many purposes adequate bond strength between webs 34 and 41 can be achieved through the application of hot-melt adhesive to web 34 only, additional bond strength can be realized by applying hot-melt adhesive to web 41 by means of a second glue nozzle 47 shown in broken lines.

Modifications may be made in the invention without departing from the spirit of it. As indicated above, various types of substrate webs may be used in the process of the present invention. The same is true with respect to the porous, fibrous web which may take the form, for example, of a wet-strength paper, a woven cloth or the like.

The process of the present invention may be used to apply an overall coating on the porous, fibrous web or a pattern coating, as described above. Various adhesive coating patterns are possible including stripes running in the machine direction, wide bands, or interrupted or intermittent patterns. It is also within the scope of the present invention to substitute gravure wipe-coating techniques for the slot extrusion orifice nozzles taught above to provide the adhesive globules on the surface fibers and fiber junctions of the porous web.

In an instance where it might not be convenient to combine the porous, fibrous web and the substrate web immediately after application of the hot-melt adhesive to the porous web, the adhesive globules can be allowed to solidify and can subsequently be reheated prior to the lamination step. In an instance where adhesive "press-through" or "strike-through" proves to be a particular problem, combiner roll 20 of FIG. 4 or combiner rolls 36 and 43 of FIG. 8 could be web-wrapped more than twice. This would entail a proper adjustment of the preset combiner nip clearance.

In the manufacture of integral disposable diapers, it will be understood by one skilled in the art that the topsheet need not be adhered to both the core and the backsheet. By appropriate pattern coating of the topsheet or the like the topsheet may be adhered to the core only or to the backsheet only.

The embodiments of the invention in which an exclusive property or privilege is claimed are defined as follows:

1. A process of continuously manufacturing integral disposable diapers of the type comprising a fluid-porous, fibrous topsheet, a fluid impermeable, non-fibrous backsheet and an absorbent core element therebetween, said process comprising the steps of providing a continuous web of fluid-porous, fibrous topsheet material and a continuous web of fluid-impermeable, non-fibrous backsheet material, providing a controlled thickness hot-melt adhesive source, causing said topsheet web to pass over said hot-melt adhesive source with some at least of the individual fibers and fiber junctions defining that surface of said top sheet web adjacent said hot-melt adhesive source wiping hot-melt adhesive from said source thereof to form randomly disposed adhesive globules on said last mentioned individual fibers and fiber junctions, providing a pair of preset clearance nip rolls, continuously passing said topsheet web and said backsheet web between said rolls with said surface of said topsheet web facing said backsheet web, continuously introducing core elements one after another in spaced relationship between said topsheet web and said backsheet web upstream of said rolls, providing a preset clearance nip gap between said rolls so sized as to deform said adhesive globules on that portion of said topsheet web adjacent said backsheet web to bond said top and back sheet webs directly together while minimizing press-through of said adhesive through said topsheet web and severing said bonded topsheet and backsheet webs to form said integral disposable diapers.

2. The process claimed in claim 1 including the steps of providing a recess filled with resilient material in the peripheral surface of that preset clearance nip roll in contact with said backsheet web, said recess being so sized and said resilient material being so chosen as to accommodate the extra thickness of said core elements between said topsheet and backsheet webs as said core elements pass between said rolls such that said adhesive globules on those portions of said topsheet web adjacent said core elements will be deformed to bond said topsheet web directly to said core elements with minimum press-through of said adhesive through said topsheet web and performing said severing of said bonded topsheet and backsheet webs between said core elements to form said integral disposable diapers.

3. The process claimed in claim 1 wherein said adhesive globules are randomly located at the positions of said surface fibers and fiber junctions over all of said surface of said topsheet web.

4. The process claimed in claim 1 wherein said adhesive globules are randomly located at the positions of said surface fibers and fiber junctions within a pattern on said surface of said topsheet web.

5. The process claimed in claim 1 wherein said controlled thickness hot-melt adhesive source comprises a slot extrusion orifice nozzle.

6. The process claimed in claim 5 including the step of pumping hot-melt adhesive through said slot extrusion orifice of said nozzle at a rate such that a uniform continuous layer of said hot-melt adhesive having a thickness of from about 0.0002 inch to about 0.0010 inch would be deposited on a non-porous, non-fibrous web moving at the same rate as said topsheet web.

7. The process claimed in claim 1 including the step of passing said topsheet web between said preset clearance nip rolls at least twice, said topsheet web being free of adhesive globules during at least its first passage between said rolls, said topsheet web having said adhesive globules on said surface thereof during its last passage between said rolls, during said last passage between said rolls said topsheet web with said adhesive globules thereon being located between said backsheet web and said globule-free portion of said topsheet web passing between said rolls whereby any adhesive pressed through said globule-bearing portion of said topsheet web by said rolls will accumulate on said globule-free portion of said topsheet web passing through said rolls.

8. A process of continuously bonding a fluid-porous, fibrous web to a substrate comprising the steps of providing a controlled thickness hot-melt adhesive source, causing said porous web to pass over said hot-melt adhesive source with some at least of the individual fibers and fiber junctions defining that surface of said porous web adjacent said hot-melt adhesive source wiping hot-melt adhesive from said source thereof to form randomly disposed adhesive globules on said last mentioned individual fibers and fiber junctions, providing a pair of preset clearance nip rolls, passing said porous web and said substrate between said rolls with said surface of said porous web adjacent said substrate and providing a preset clearance nip gap between said rolls so sized as to deform said adhesive globules and minimize press-through of said adhesive through said porous web.

9. The process claimed in claim 8 wherein said adhesive globules are randomly located at the positions of said surface fibers and fiber junctions over all of said surface of said porous web.

10. The process claimed in claim 8 wherein said adhesive globules are randomly located at the positions of said surface fibers and fiber junctions within a pattern on said surface of said porous web.

11. The process claimed in claim 8 wherein said controlled thickness hot-melt adhesive source comprises a slot extrusion orifice nozzle.

12. The process claimed in claim 11 including the step of pumping hot-melt adhesive through said slot extrusion orifice of said nozzle at a rate such that a uniform continuous layer of said hot-melt adhesive having a thickness of from about 0.0002 inch to about 0.0010 inch would be deposited on a non-porous, non-fibrous web moving at the same rate as said porous web.

13. The process claimed in claim 8 including the step of passing said porous web between said preset clearance nip rolls at least twice, said porous web being free of adhesive globules during at least its first passage between said rolls, said porous web having said adhesive globules on said surface thereof during its last passage between said rolls, during said last passage between said rolls said porous web with said adhesive globules thereon being located between said substrate and said globule-free portion of said porous web passing between said rolls whereby any adhesive pressed through said globule bearing portion of said porous web by said rolls will accumulate on said globule-free portion of said porous web passing through said rolls.

14. The process claimed in claim 13 wherein said substrate comprises a porous, fibrous web and including the step of passing said substrate web between said preset clearance nip rolls at least twice whereby any hot-melt adhesive pressed through said portion of said substrate web passing last through said rolls will accumulate on an adjacent portion of said substrate web.

* * * * *